US012152055B2

(12) United States Patent
Dunning et al.

(10) Patent No.: US 12,152,055 B2
(45) Date of Patent: *Nov. 26, 2024

(54) SYSTEMS FOR REMOVAL OF DETERGENTS FROM AQUEOUS SOLUTIONS

(71) Applicant: BioMadison, Inc., Del Mar, CA (US)

(72) Inventors: Francis Mark Dunning, Madison, WI (US); Ward C. Tucker, Monona, WI (US)

(73) Assignee: BioMadison, Inc.

(*) Notice: Subject to any disclaimer, the term of this patent is extended or adjusted under 35 U.S.C. 154(b) by 71 days.

This patent is subject to a terminal disclaimer.

(21) Appl. No.: 18/094,663

(22) Filed: Jan. 9, 2023

(65) Prior Publication Data

US 2023/0143149 A1    May 11, 2023

Related U.S. Application Data

(63) Continuation of application No. 16/818,678, filed on Mar. 13, 2020, now Pat. No. 11,578,099.

(60) Provisional application No. 62/818,554, filed on Mar. 14, 2019.

(51) Int. Cl.
C07K 1/34       (2006.01)
B01D 15/34      (2006.01)
B01D 61/14      (2006.01)
B01D 61/16      (2006.01)
G01N 33/68      (2006.01)

(52) U.S. Cl.
CPC ............... C07K 1/34 (2013.01); B01D 15/34 (2013.01); B01D 61/145 (2013.01); B01D 61/16 (2013.01); G01N 33/6803 (2013.01); B01D 2311/12 (2013.01)

(58) Field of Classification Search
CPC ........ C07K 1/34; B01D 15/34; B01D 61/145; G01N 33/6803
See application file for complete search history.

(56) References Cited

U.S. PATENT DOCUMENTS 5,772,888 A        6/1998   Liu
2005/0170519 A1    8/2005   Alam
2008/0308495 A1    12/2008  Somasundaran

FOREIGN PATENT DOCUMENTS

WO    03080651       10/2003
WO    2015059478     4/2015

OTHER PUBLICATIONS

Rangel-Yagui, et al. "Two-Phase Aqueous Micellar Systems—an Alternative Method for Protein Purification," Brazilian Journal of Chemical Engineering. vol. 21, No. 04, pp. 531-544, Oct.-Dec. 2004. 14 pages.

Primary Examiner — Sikarl A Witherspoon
(74) Attorney, Agent, or Firm — Fish IP Law, LLP

(57) ABSTRACT

Systems are described in which a primary detergent or surfactant in an aqueous solution is removed by the addition of a secondary detergent or surfactant in concentrations that exceed the critical micellar concentration (CMC) of the secondary detergent or surfactant using a size separation device. These systems are particularly applicable to protein-containing solutions. Typical primary detergents/surfactants include polysorbate 20, polysorbate 80, and Triton X-100. Suitable secondary detergents or surfactants can be ionic, nonionic, or zwitterionic. Typical secondary detergents/surfactants include, but are not limited to, galactoside detergents (e.g. octyl-β-galactoside), glucamide detergents (e.g. MEGA 8, MEGA 9, MEGA 10), cholamide detergents (e.g. CHAPS, CHAPSO, BIGCHAPS), and sulfobetaine detergents (such as sulfobetaine 3-10).

11 Claims, 23 Drawing Sheets

Undialyzed

EC$_{50}$(pM)
0.99

- BoNT/A holotoxin
- BoNT/A +P80 y-axis: emission ratio (Em 526/Em 470)
x-axis: log [BoNT/A holotoxin]. pM / log [BoNT/A + P80]. U

FIG. 9A

Dialyzed

EC$_{50}$
0.72 pM
32 U/ml

- BoNT/A holotoxin
- BoNT/A +P80 y-axis: emission ratio (Em 526/Em 470)
x-axis: log [BoNT/A holotoxin]. pM / log [BoNT/A + P80]. U

FIG. 9B

Control (No 2° Detergent)   Octyl-β-glucoside   Mega 8   Mega 9   Mega 10

BigCHAPs   Deoxycholate   CHAPs   Mock Placebo (No Filter)   cBAM2, No PS80 (No Filter)

*FIG. 9C*

- ● BoNT/A +P80
- □ BoNT/A holotoxin

*FIG. 9D*

Neurobasal Control  Neurobasal +P80 Control

O/N HSA
0% Sample HSA  O/N HSA
0.1% Sample HSA

SYSTEMS FOR REMOVAL OF DETERGENTS FROM AQUEOUS SOLUTIONS

This application is a continuation of U.S. patent application Ser. No. 16/818,678, filed Mar. 13, 2020, which claims the benefit of U.S. Provisional Patent Application No. 62/818,554 filed on Mar. 14, 2019. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is detergent or surfactant removal, particularly from pharmaceutical preparations.

BACKGROUND

The following description includes information that may be useful in understanding the present invention. It is not an admission that any of the information provided herein is prior art or relevant to the presently claimed invention, or that any publication specifically or implicitly referenced is prior art.

Excipients are frequently added to small molecule (e.g. <500 D) and/or protein solutions (such as pharmaceutical preparations) in order to reduce aggregation, prevent non-specific binding to container surfaces, and otherwise improve stability. Conventional excipients include proteins (such as human or bovine serum albumin, ovalbumin, immunoglobulins, etc.), sugars and polysaccharides, and soluble polymers (such as polyvinylpyrrolidone). In an attempt to provide non-immunogenic formulations, non-ionic and zwitterionic detergents and surfactants are increasingly being used for this purpose. Many detergents and surfactants, however, interfere with analytical methods used for characterization and/or quality control of such solutions (such as immunoassays, peptide reporter-based assays, cell based assays, mass spectrometry, etc.).

Unfortunately, detergents and surfactants can be problematic to remove from solution once introduced. Ion exchange can be used for removal of charged (e.g. cationic or anionic) detergents and surfactants, however many surfactants in common use do not carry a formal charge. Hydrophobic media can bind large amounts of detergent and/or surfactant, however such hydrophobic media can also bind significant amounts of the protein of interest (which may be present in low concentrations). Dialysis is used for detergent or surfactant removal with only partial success, as self-association of detergents or surfactants into micelles reduces the amount of "solvated" surfactant or detergent available for removal by dialysis. As a result, concentration gradient driven dialysis for removal of detergents and surfactants is very slow. The formation of micelles also interferes with efforts to remove surfactants and detergents by more active size-based separation methods, such as gel filtration and ultrafiltration, as their size leads to retention by ultrafiltration membranes and exclusion from the internal volume of gel filtration media.

Commercial products are available for removal of surfactants and detergents from aqueous solutions. For example, ThermoFisher's HiPPR resin purports to remove 95% of surfactant or detergent from low concentration protein/peptide solutions while maintaining protein/peptide content. G Biosciences offers a DetergentOUT™ resin described as having a high affinity for most surfactants and a low affinity for most proteins and peptides. Calbiochem provides a hydrophobic CALBIOSORB™ resin for use in batchwise removal of surfactants, and suggests using the resin in a dialysis buffer in order to avoid nonspecific binding of proteins of interest. It is not clear, however, if such products are effective in removal of the polysorbate surfactants that are increasingly being used as excipients or if all proteins/peptides are retained in solution following treatment.

Extraction of peptide solutions using organic solvents, such as ethyl acetate, is utilized in some applications. In such extractions the relatively hydrophobic detergent transfers to the relatively insoluble organic layer of the extraction mixture. Due to the possibility of irreversible denaturation, however, such methods are generally followed by characterization of physical properties of the protein (for example, by mass spectrometry) that may not be informative in regard to activity.

Thus, there is still a need for a simple and convenient method for removal detergents and/or surfactants from aqueous solutions, while retaining functional proteins and/or peptides in the solution.

SUMMARY OF THE INVENTION

Compositions and methods of the inventive concept provide methods for removing a surfactant or detergent (e.g. polysorbate 20, polysorbate 80, and/or Triton X-100) from a protein-containing solution comprising a protein by directly adding a second surfactant or detergent (e.g. a galactoside detergent such as octyl-β-galactoside; a glucamide detergent such as MEGA 8, MEGA 9, and/or MEGA 10; a cholamide detergent such as CHAPS, CHAPSO, and/or BIGCHAPS; and/or a sulfobetaine detergent such as sulfobetaine 3-10) to the solution to give a concentration at least equal to the second surfactant or detergent critical micellar concentration, allowing mixed micelles that include both of the surfactants/detergents to form, and separating the protein from the resulting mixed micelles using a size-based separation method (such as ultrafiltration and/or gel filtration). Some embodiments include a step of blocking an ultrafiltration membrane utilized in an ultrafiltration separation prior to or at the time of separating the protein from the mixed micelles. Some embodiments include a step of blocking a gel filtration media utilized in a gel filtration separation prior to or at the time of separating the protein from the mixed micelles. Some embodiments of the inventive concept include a step of collecting an analysis fraction that includes the protein from the size-based separation method, which can be analyzed using a cell-based assay. The protein can be a *Botulinum* neurotoxin (e.g. Botulinum neurotoxin serotype A or BoNT/A).

BRIEF DESCRIPTION OF THE DRAWINGS

FIG. 1: FIG. 1 schematically depicts an exemplary process for detergent removal from a protein-containing solution FIG. 2: FIG. 2 shows typical results of CMC 535™ characterization of detergent content of aqueous solutions treated with different primary and secondary detergents.

FIG. 3A shows typical results for removal of Polysorbate 20 from solution using diafiltration in the presence of different secondary detergents. FIG. 3B show typical results for removal of Polysorbate 80 from solution using diafiltration in the presence of different secondary detergents. FIG. 3C shows typical results for removal of Triton X-100 from solution using diafiltration in the presence of different secondary detergents.

FIG. 4A shows typical results for Botulinum neurotoxin serotype A (BoNT/A) from solution using a method of the inventive concept. The upper panel shows BoNT/A recovery from a BoNT/A sample containing polysorbate 20. The lower panel shows the same data normalized relative to a control sample containing BoNT/A and no primary detergent (polysorbate 20). FIG. 4B shows typical results for Botulinum neurotoxin serotype A (BoNT/A) from solution using a method of the inventive concept. The upper panel shows BoNT/A recovery from a BoNT/A sample containing polysorbate 80. The lower panel shows the same data normalized relative to a control sample containing BoNT/A and no primary detergent (polysorbate 80). FIG. 4C shows typical results for Botulinum neurotoxin serotype A (BoNT/A) from solution using a method of the inventive concept. The upper panel shows BoNT/A recovery from a BoNT/A sample containing Triton X-100. The lower panel shows the same data normalized relative to a control sample containing BoNT/A and no primary detergent (Triton X-100).

FIG. 5A shows typical results from studies of the effect of additional BigCHAP washes on removal of polysorbate 80, determined using the CMC 535™ method. FIG. 5B shows typical results from studies of the effect of additional buffer washes on removal of a polysorbate 80, determined using the CMC 535™ method.

FIG. 6A shows typical results from studies of BoNT/A recovery from samples containing polysorbate 80, which was subsequently removed using mixed micellar extraction with BigCHAP and with application of repeated washes with buffer containing BigCHAP. The upper panel shows results relative to BoNT/A added to the sample. The lower panel shows results relative to recovery from a BoNT/A sample that did not contain polysorbate 80. FIG. 6B shows typical results from studies of BoNT/A recovery from samples containing polysorbate 80, which was subsequently removed using mixed micellar extraction with BigCHAP with application of repeated washes with buffer that did not include a secondary detergent. The left panel shows results relative to BoNT/A added to the sample. The right panel shows results relative to recovery from a BoNT/A sample that did not contain polysorbate 80.

FIG. 7A shows typical results of extraction of polysorbate 20 from BoNT/A samples using octyl-β-galactoside (OBG), BigCHAP, or CHAPS at different concentrations, as characterized using the CMC 535™ method. FIG. 7B shows typical results of extraction of polysorbate 80 from BoNT/A samples using octyl-β-galactoside (OBG), BigCHAP, or CHAPS at different concentrations, as characterized using the CMC 535™ method. FIG. 7C shows typical results of extraction of Triton X-100 from BoNT/A samples using octyl-β-galactoside (OBG), BigCHAP, or CHAPS at different concentrations, as characterized using the CMC 535™ method.

FIG. 8A shows typical results from studies of recovery of BoNT/A from samples containing polysorbate 20 following mixed micelle extraction with octyl-β-galactoside (OBG), BigCHAP, or CHAPS at different concentrations, as characterized using the BioSentinel BoTest A/E reagent. The upper panel shows BoNT/A recovery as a percentage of the amount added. The lower panel shows BoNT/A recovery as a percentage of recovery of a control BoNT/A sample that did not contain polysorbate 20. FIG. 8B shows typical results from studies of recovery of BoNT/A from samples containing polysorbate 80 following mixed micelle extraction with octyl-β-galactoside (OBG), BigCHAP, or CHAPS at different concentrations, as characterized using the BioSentinel BoTest A/E reagent. The upper panel shows BoNT/A recovery as a percentage of the amount added. The lower panel shows BoNT/A recovery as a percentage of recovery of a control BoNT/A sample that did not contain polysorbate 80. FIG. 8C shows typical results from studies of recovery of BoNT/A from samples containing Triton X-100 following mixed micelle extraction with octyl-β-galactoside (OBG), BigCHAP, or CHAPS at different concentrations, as characterized using the BoTest™ A/E reagent. The upper panel shows BoNT/A recovery as a percentage of the amount added. The lower panel shows BoNT/A recovery as a percentage of recovery of a control BoNT/A sample that did not contain Triton X-100.

FIGS. 9A to 9D: FIG. 9A shows typical results obtained from a cell-based BoNT/A assay performed using BoNT/A prepared in either surfactant-free media or media containing a polysorbate 80 excipient. FIG. 9B shows typical results from studies similar to those of FIG. 9A, in which BoNT/A samples were dialyzed prior to assay. FIG. 9C shows typical results from studies of the use of secondary surfactants to remove an polysorbate 80 excipient from BoNT/A containing samples, specifically the effects of the polysorbate 80 excipient and residual surfactant in samples extracted with secondary surfactants on the morphology of cells used in the BioSentinel BoTest™ A/E assay. FIG. 9D shows typical results from EC50 determinations for BoNT/A in the BioSentinel BoTest™ A/E assay performed using BoNT/A prepared in surfactant-free media and BoNT/A prepared in media containing a polysorbate 80 excipient and subjected to mixed micelle extraction.

FIG. 10 shows typical results of studies of the retention of mixed micelles of polysorbate 80 and BigCHAP by Amicon regenerated cellulose ultrafiltration membranes with different molecular weight cutoffs (MWCs).

FIG. 11 shows a comparison of the retention of mixed micelles of polysorbate 80 and BigCHAP through PES (Pierce, Sartoris) ultrafiltration membranes with different MWCs.

FIG. 12 shows typical results of studies of the recovery of BoNT/A following mixed micelle removal of polysorbate 80 by BigCHAPS, using regenerated cellulose (Amicon) and PES (Pierce, Sartoris) ultrafiltration membranes with various molecular weight cutoffs.

FIG. 13 shows typical results from studies of the effect of human serum albumin (HSA) preblocking and combined preblocking and sample spiking on the recovery of primary detergent and BoNT/A following mixed micelle separation.

FIG. 14 show typical results from studies of the effect of human serum albumin (HSA) preblocking and combined preblocking and sample spiking on cells used in the BioSentinel in vivo BoCell™ assay.

DETAILED DESCRIPTION

Figure 3A:
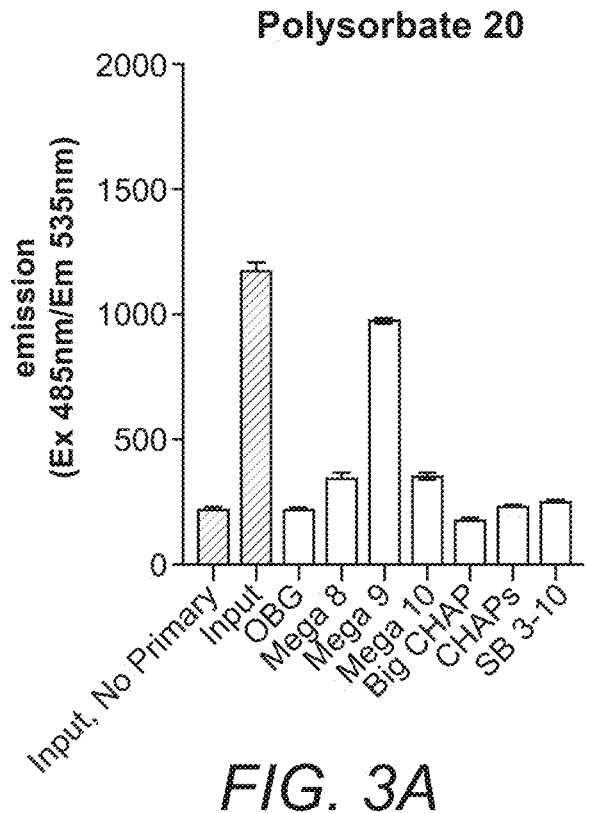
FIGS. 3A to 3C.

The inventive subject matter provides compositions and methods in which a primary detergent or surfactant (such as a detergent or surfactant added as an excipient in a protein or peptide solution) is at least partially removed by direct addition of a secondary detergent or surfactant in concentrations that exceed the critical micellar concentration (CMC) of the secondary detergent or surfactant. Secondary detergents or surfactants can be selected to form micelles with low molecular weight (e.g. less than about 500 kD, 200 kD, 150 kD, or 100 kD) and/or small hydrodynamic radius (e.g. a hydrodynamic radius smaller than that of a protein of interest). In preferred embodiments the secondary detergent of surfactant has a CMC of about 3.5 mM to about 40 mM, and/or forms micelles having a mean molecular weight ranging from about 8 kD to about 40 kD. Typical primary detergents/surfactants include, but are not limited to, polysorbate 20, polysorbate 80, and Triton X-100. Suitable secondary detergents or surfactants can be ionic, nonionic, or zwitterionic. Typical secondary detergents/surfactants include, but are not limited to, galactoside detergents (e.g. octyl-β-galactoside), glucamide detergents (e.g. MEGA 8, MEGA 9, MEGA 10), cholamide detergents (e.g. CHAPS, CHAPSO, BIGCHAPS), and sulfobetaine detergents (such as sulfobetaine 3-10).

Within the context of this application the term "about" defines a range of within 20% of the nominal value.

The secondary detergent or surfactant can be selected so as to provide no interference or acceptable levels of interference (e.g. a level of interference that does not interfere with accurate characterization) with subsequent assays for characterization of the protein or peptide, such as an immunoassay and/or a cell based assay. On direct addition of the secondary detergent or surfactant to a solution containing a primary detergent or surfactant, molecules of the primary detergent or surfactant are incorporated into micelles of the secondary detergent or surfactant to form mixed micelles containing both surfactant/detergent species. Surprisingly, the Inventors have found that secondary detergent/surfactant species and their concentration can be selected to form mixed micelles that are relatively small. Specifically, a secondary detergent or surfactant can be selected such that direct addition to a solution that includes a primary detergent or surfactant results in the formation of mixed micelles that have an effective hydrodynamic radius that is smaller than that of a protein or peptide to be analyzed (e.g. a Botulinum neurotoxin) and is present in the initial solution. It should be appreciated that surfactants and/or detergents are utilized can be present as excipients that are used to reduce aggregation of protein therapeutic drugs in many pharmaceutical formulations.

The resulting small mixed micelles can be efficiently separated and/or segregated from the protein or analyte of interest by size-based separation methods (e.g. ultrafiltration, gel filtration, etc.), thereby removing at least a portion of the primary and secondary detergents from the protein-containing solution. It should be appreciated that in some embodiments, for example those incorporating ultrafiltration, the protein or peptide of interest can be concentrated relative to the concentration in the original sample volume during the detergent/surfactant removal process. In a preferred embodiment of the inventive concept sufficient primary detergent/surfactant and secondary detergent/surfactant are removed to reduce or eliminate interference with downstream analytical methods for characterizing protein mass and/or activity. The resulting high molecular weight fraction (e.g. the retentate or flowthrough fraction) that includes the protein or peptide can then be characterized using methods that would otherwise be interfered with by the presence of the primary and/or secondary surfactant or detergent.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

In some embodiments mixed micelles of the inventive concept can pass through membranes (e.g. ultrafiltration or diafiltration membranes) that retain Botulinum neurotoxins, removing the primary surfactant from a Botulinum neurotoxin solution while retaining the active protein. Similarly, mixed micelles of the inventive concept can enter the internal volume of an appropriately selected size exclusion chromatography media, where a protein or peptide of interest in solution is excluded and appears in an the excluded (i.e. flow-through) volume and/or an early fraction during size exclusion column chromatography.

In some embodiments, for example where the concentration of protein or peptide to be characterized is low, surfaces of a membrane or gel filtration media can be blocked prior to and/or during the separation step. Such surfaces can, for example, be blocked by the addition of one or more exogenous protein(s) (e.g. human serum albumin, bovine serum albumin, avian serum albumin, an acetylated albumin, ovalbumin, mammalian immunoglobulins, avian immunoglobulins, mammalian or teleost gelatin, casein etc.) that do not interfere in downstream characterization methods. In some embodiments such surfaces can be blocked by the addition of long chain polymers such as polyvinylpyrrolidone or polyethylene glycol. Such blocking can reduce or eliminate losses due to denaturation of the analyte on separation surfaces and/or losses due to nonspecific binding to separation surfaces. Blocking proteins and/or polymers can be applied at concentrations ranging from 0.1% to 10% (w/v), and can be applied prior to, during, or both prior to and during a separation step. In some embodiments a blocking protein and/or polymer can be applied to a surface of a size separation membrane or media prior to use, given time to block the surface, and excess material removed by rinsing or washing prior to application of an analyte-containing sample.

Figures 1, 2:
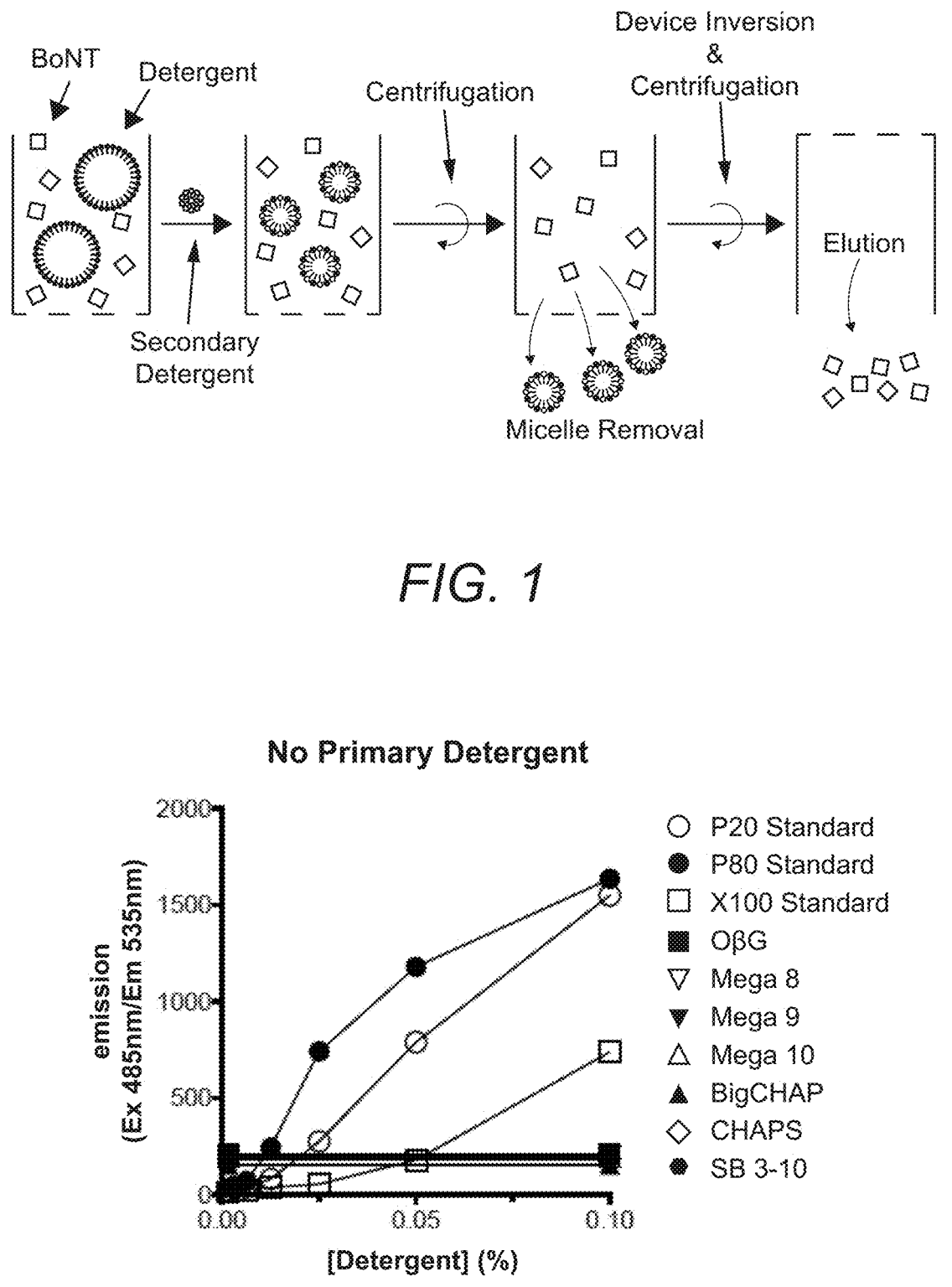

An example of a method of the inventive concept is provided in the diagram shown in FIG. 1, which depicts the use of an ultrafiltration membrane spin column for separation of the mixed micelles from a solution containing a Botulinum neurotoxin (BoNT). As shown, a secondary detergent is added directly to a BoNT provided in a solution that also includes a primary detergent, thereby forming mixed micelles with reduced hydrodynamic radius relative to those formed by the primary detergent alone. Centrifugation in a spin column fitted with an ultrafiltration membrane having an appropriate molecular weight cutoff results in passage of the mixed micelles through the membrane and retention of the BoNT. The retained BoNT-containing solution is readily recovered by reversing the orientation of the sample-containing portion of the spin column and brief centrifugation. It should be appreciated that recovery of the BoNT in a smaller volume than that of the applied sample can provide concentration of the BoNT, which can facilitate analysis (for example, using a cell-based or immunological assay).

The Inventors have found that methods of the inventive concept are effective in removing primary surfactants that interfere in biochemical characterization methods and cell-based methods. The Inventors believe that methods of the inventive concept can similarly be applied to physical methods such as mass spectrometry and capillary electrophoresis.

In a typical surfactant/detergent removal protocol an Amicon UFC spin column is pre-blocked using a blocking buffer containing 0.5% w/v human serum albumin (HSA), with residual blocking buffer removed by centrifugation. 100 µL of a test sample or drug product (for example, 100 pM Botulinum neurotoxin serotype A (BoNT/A) in 50 mM HEPES, 140 mM NaCl, 0.5% HSA (human serum albumin), and 0.1% primary detergent) is then mixed with 400 µL of a buffer containing a secondary detergent at a concentration selected to match or exceed the CMC of the secondary detergent (e.g. about 1% w/v or higher) after mixing. In some embodiments HSA is omitted, having been found to reduce recovery of some BoNT species (e.g. BoNT/A).

After a brief incubation period (e.g. about one minute. two minutes, three minutes, five minutes, ten minutes, fifteen minutes, thirty minutes, or one hour) the mixture is applied to the spin column and centrifuged. In some embodiments the spin column can be washed by adding 500 µL volumes of a buffer containing the secondary detergent and applying centrifugal force. After washing the spin column with 500 µL of a wash buffer the spin column is inverted and centrifuged briefly to recover an approximately 15 µL volume representing the detergent-extracted sample. This volume can be diluted for analysis and/or splitting between different analytical methods.

As shown in FIG. 2, Inventors have found that a commercial product utilized for characterizing detergent concentration (CMC 535™) is nonreactive with many of the detergents that have been found to be useful as secondary detergents. As shown, the CMC 535™ assay generates a dose/response curve with polysorbate 20 (P20), polysorbate 80 (P80), and Triton X-100 (X100), but has no apparent response to a number of potential secondary detergents within the tested range of concentrations.

Figure 3B:
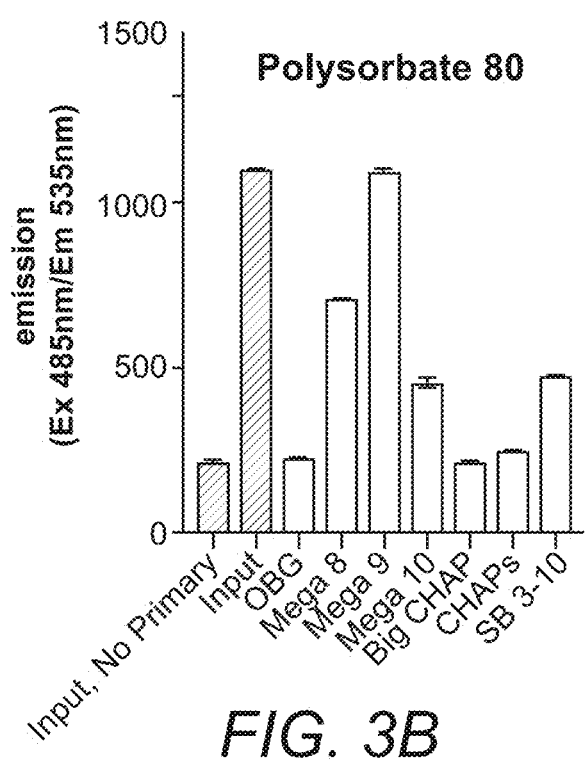
Figure 3C:
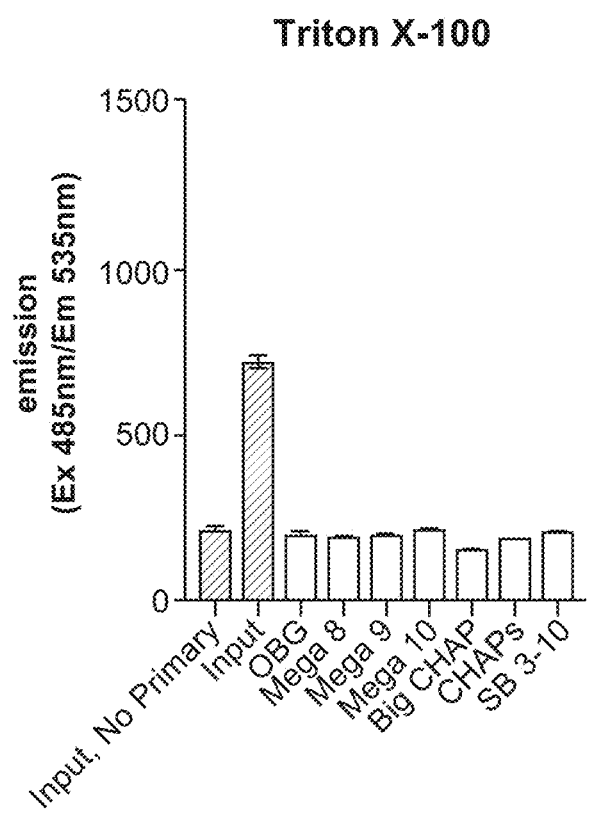

Typical results for primary detergent removal using the above protocol and characterized using CMC 535™ are shown in FIGS. 3A to 3C. As shown, octyl-β-glucoside, BigCHAP, and CHAPS work well to remove polysorbate detergents. Triton X-100 removal appears to be independent of the selection of secondary detergent.

Figure 4A:
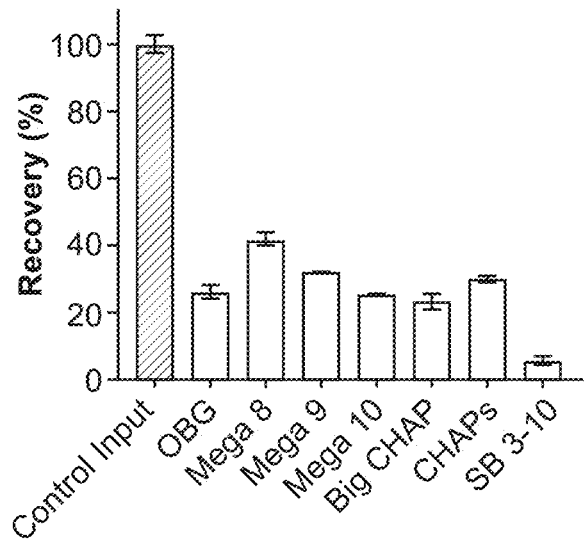
FIGS. 4A to 4C.
Figure 4A:
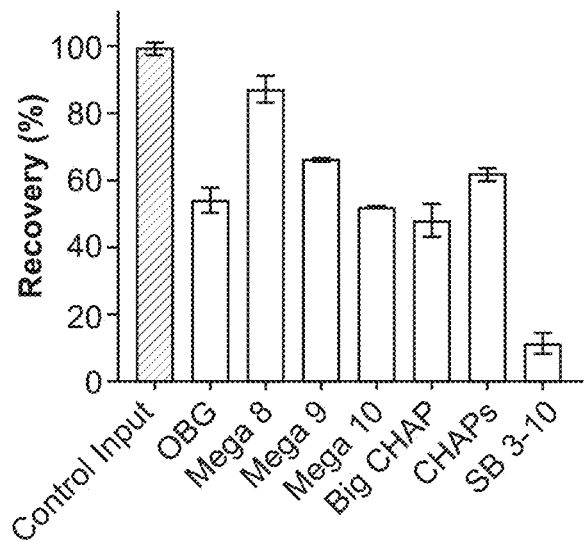
Figure 4B:
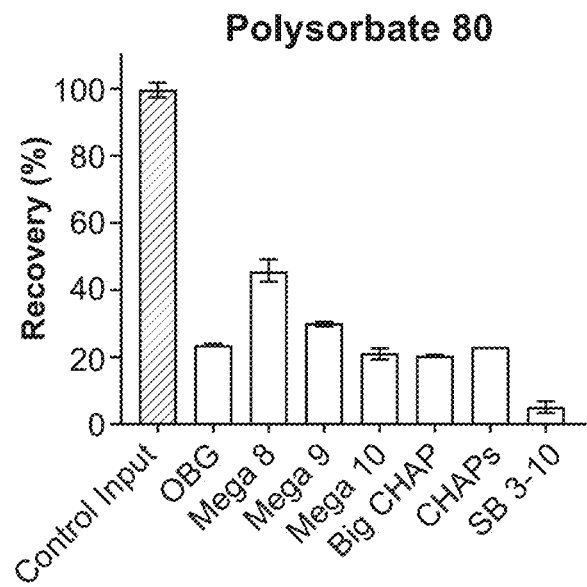
Figure 4B:
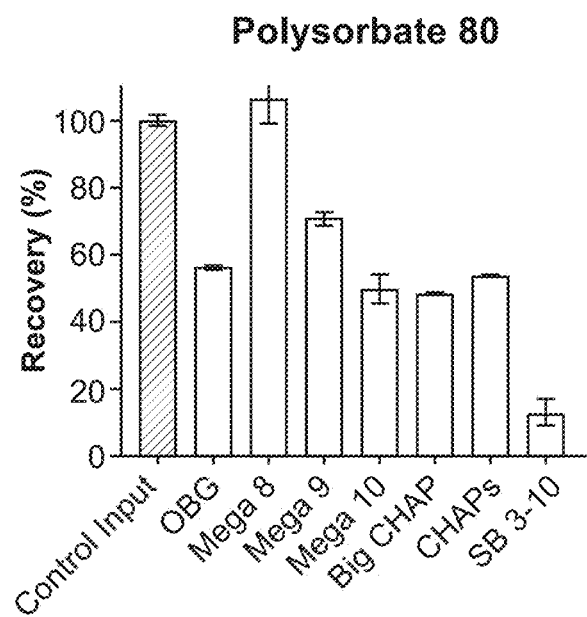
Figure 4C:
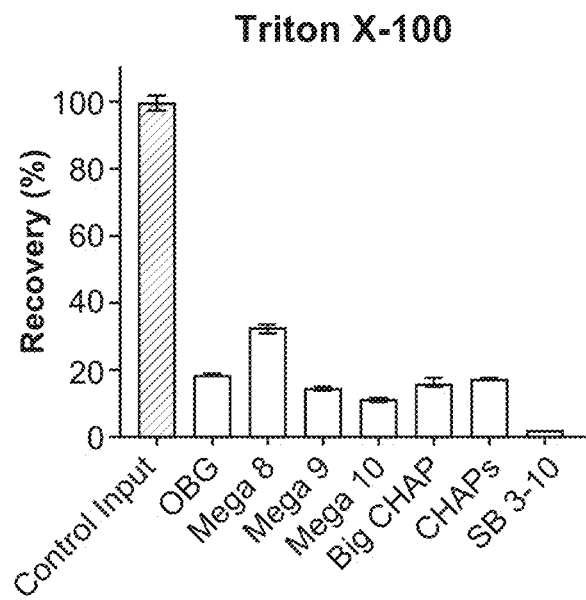
Figure 4C:
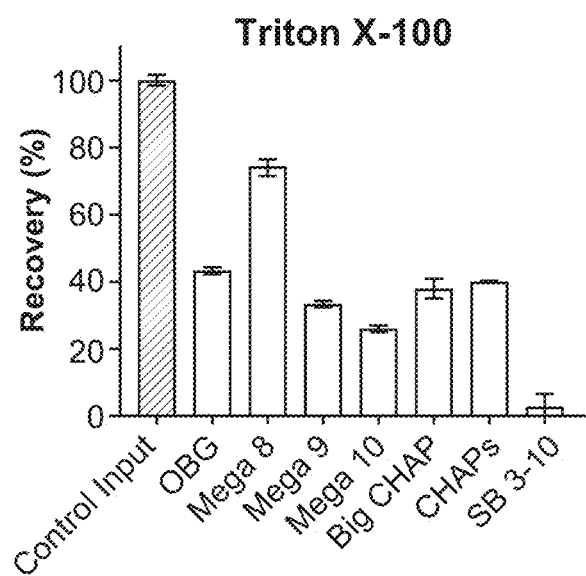

Test samples containing BoNT/A in buffers containing a primary surfactant were similarly treated, and the BoNT/A content characterized using the BioSentinel BoTest™ activity assay. The BoTest™ activity assay utilizes a reporting peptide that incorporates an analog of the BoNT/A substrate, with a FRET pair of fluorophores separated by a substrate peptide. Proteolysis results in separation of the FRET pair and an observable change in fluorescence. The in vitro BoTest™ assay was performed by mixing 50 µL of extracted sample with 100 µL of 0.25 µM BoTest™ A/E reporting peptide substrate and quantified using a BoNT/A dose/response curve. Results are shown in FIGS. 4A to 4C. It should be appreciated that in some instances primary detergents can activate BoNT/A to some extent. Accordingly, control samples that retain the primary detergent can show a falsely elevated BoNT/A activity that gives the impression of low recovery following mixed micelle removal of the primary detergent in test samples. Similarly, when a control is provided without primary detergent recovery may be overestimated. Nevertheless, improved recovery of BoNT/A with certain secondary detergents is evident. As shown, the selection of secondary detergent can have an effect on recovery of BoNT/A. For example, the detergent SB-10 may be incompatible with the BoTest™ testing methodology.

Figure 5A:
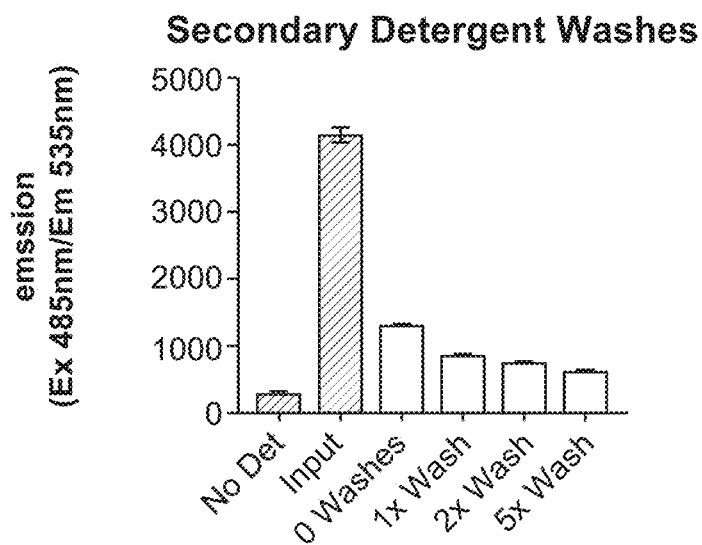
FIGS. 5A and 5B.
Figure 5A:
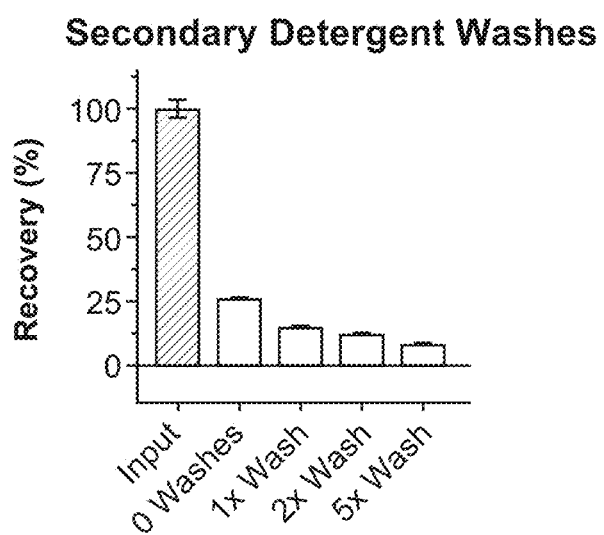
Figure 5B:
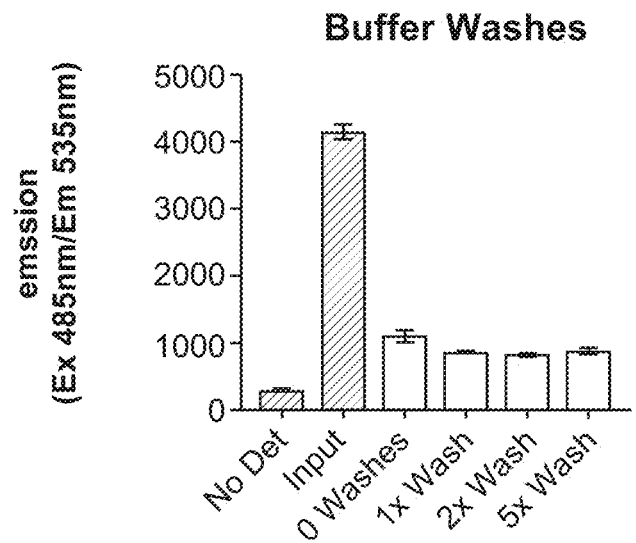
Figure 5B:
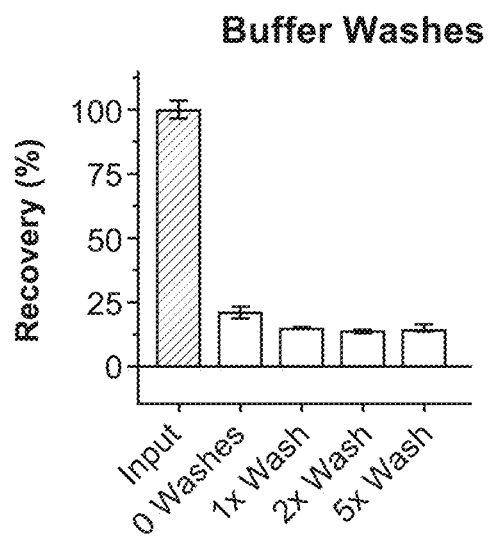

In some embodiments additional volumes of buffer containing a secondary detergent (BigCHAP) can be applied to a sample containing BoNT/A and a primary detergent (polysorbate 80), followed by additional rounds of centrifugation. As shown in FIG. 5A, this can be effective in providing further removal of the primary detergent as shown by CMC 35™ testing. FIG. 5B shows the effect of similar studies using buffer without the secondary surfactant. As shown, additional washing with secondary detergent-containing buffers can remove additional primary detergent that is not removed in an initial mixed micelle extraction. Additional washes with buffer do not provide this effect.

Figure 6A:
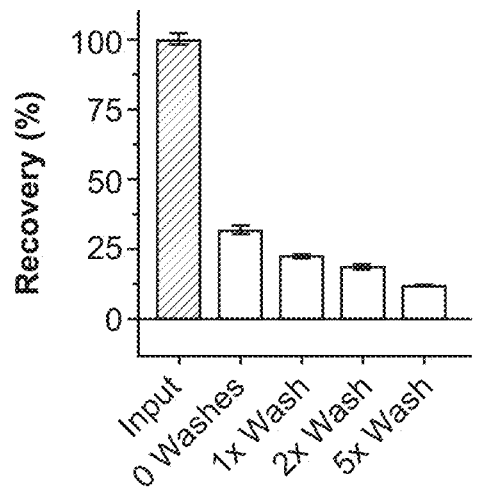
FIGS. 6A and 6B.
Figure 6A:
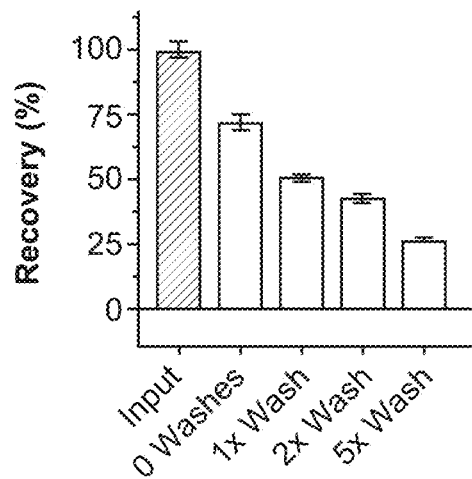
Figure 6B:
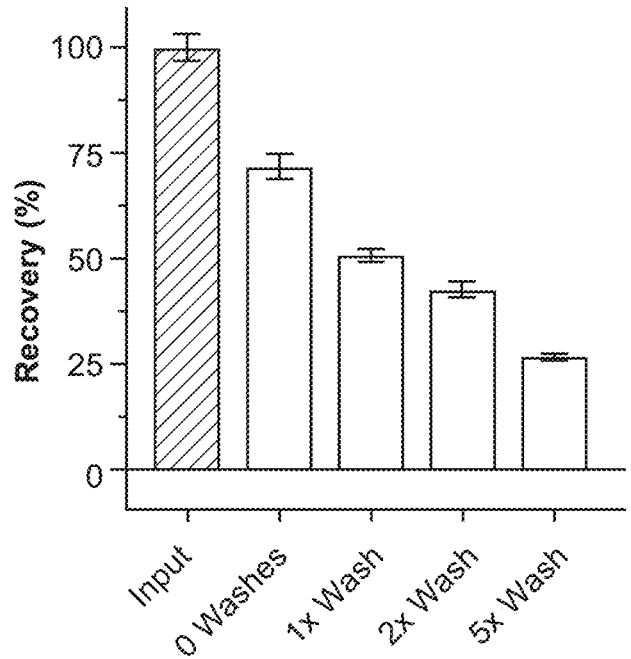
Figure 6B:
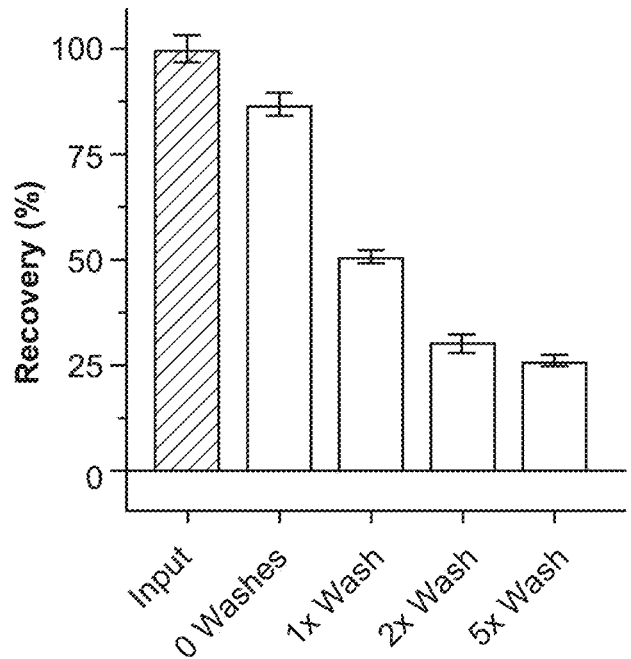

It should be appreciated that improved extraction of primary detergent does not necessarily indicate improved performance in functional analyte recovery. The samples evaluated above in FIGS. 5A and 5B were also characterized using the BoTest™ A/E reagent as described above. Results are shown in FIGS. 6A and 6B. As shown, recovery of functional BoNT/A decreases with additional washes. This may be due to denaturation and/or loss of BoNT/A due to nonspecific binding. Accordingly, mixed micelle extraction protocols can be adapted for optimal recovery of functional analyte, which may or may not correlate with the most effective protocol for removal of primary detergent. In some embodiments additional washes following initial mixed micelle extraction can be eliminated.

Figure 7A:
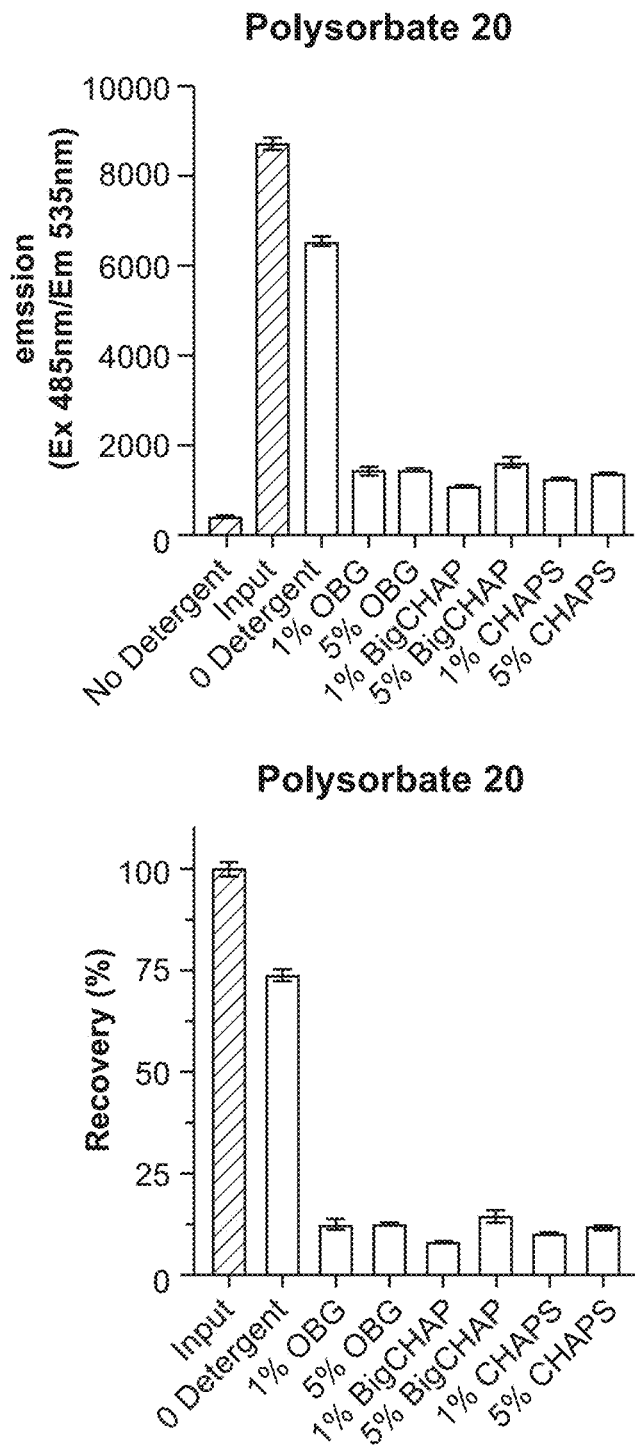
FIGS. 7A to 7C.
Figure 7B:
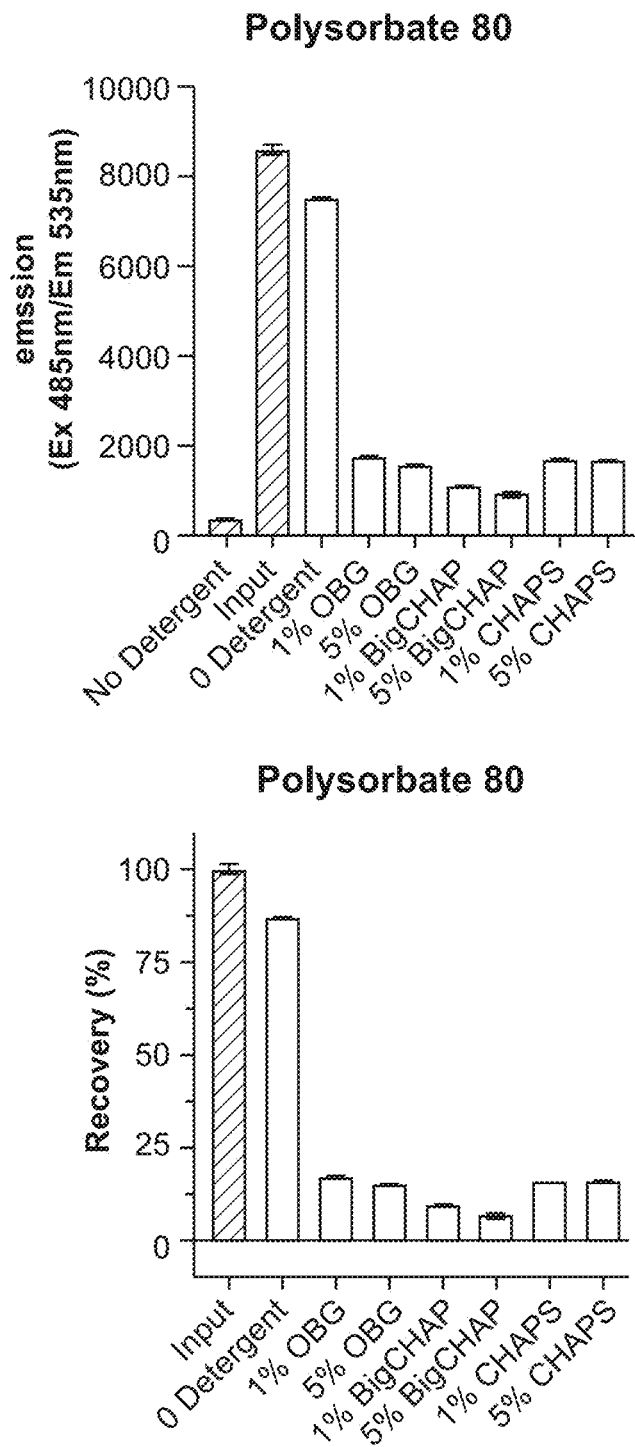
Figure 7C:
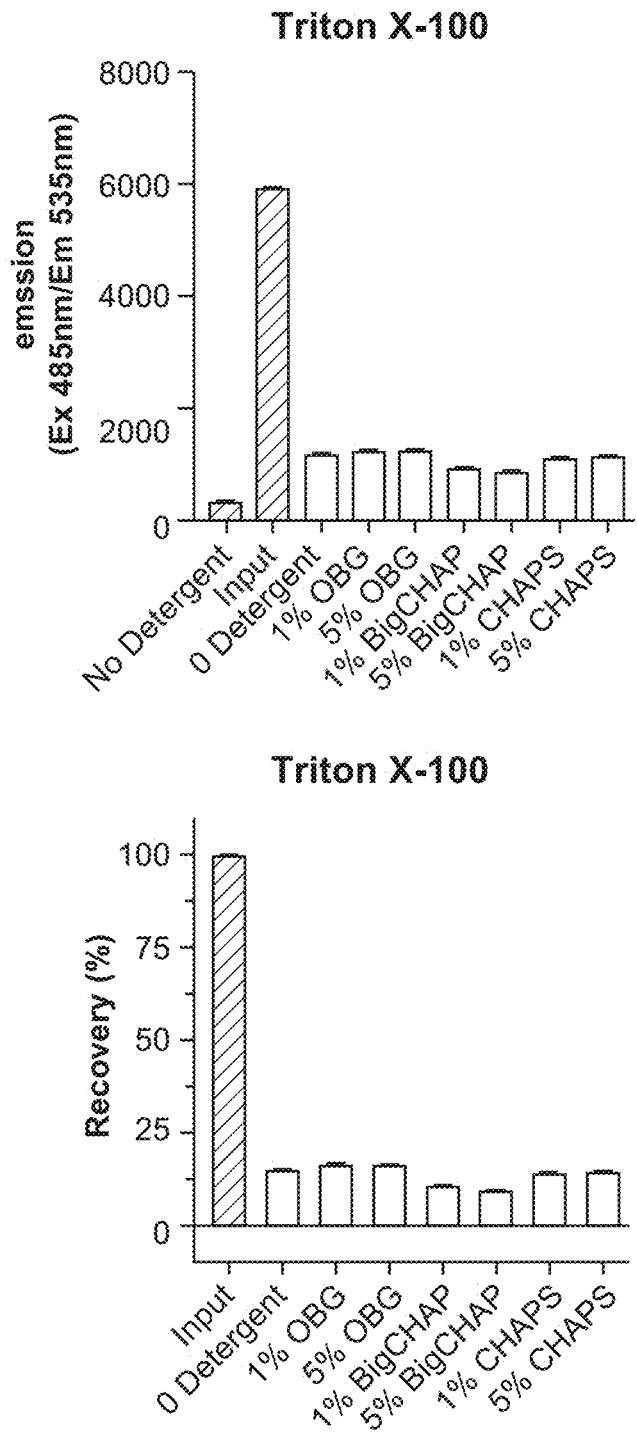

FIGS. 7A to 7C show the results of optimized mixed micelle extraction protocols developed for BoNT/A samples containing polysorbate 20, polysorbate 80, and Triton X-100 primary detergents, and using octyl-β-galactoside, Big-CHAP, and CHAPS as secondary detergents, as characterized using CMC 535™ (i.e. detection of residual primary detergent). Spin columns were pre-blocked with human serum albumin prior to use; human serum albumin was also added to the BoNT/A preparations. Surprisingly, Inventors have found that some primary detergents (e.g. Triton X-100) appear to be able to be removed from samples by diafiltration without the need for formation of mixed micelles. As shown, there is no significant difference between the use of 1% (w/v) and 5% (w/v) secondary detergent in the removal of primary detergents as determined using CMC 535™.

Figure 8A:
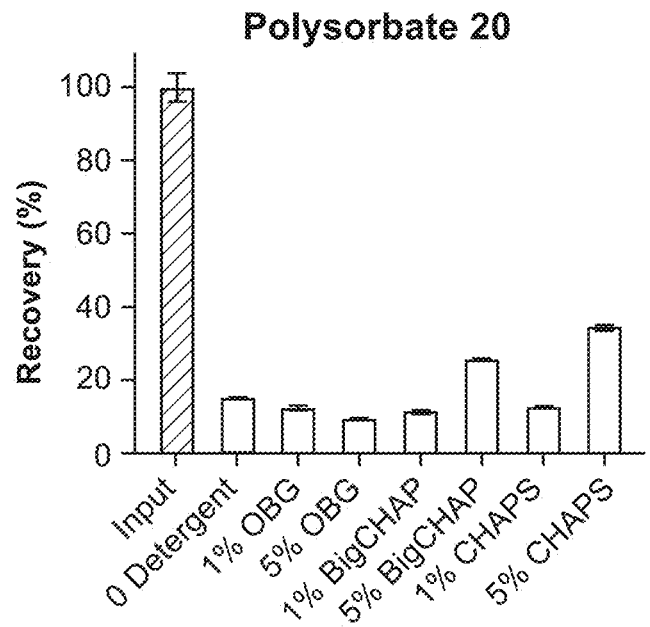
FIGS. 8A to 8C.
Figure 8A:
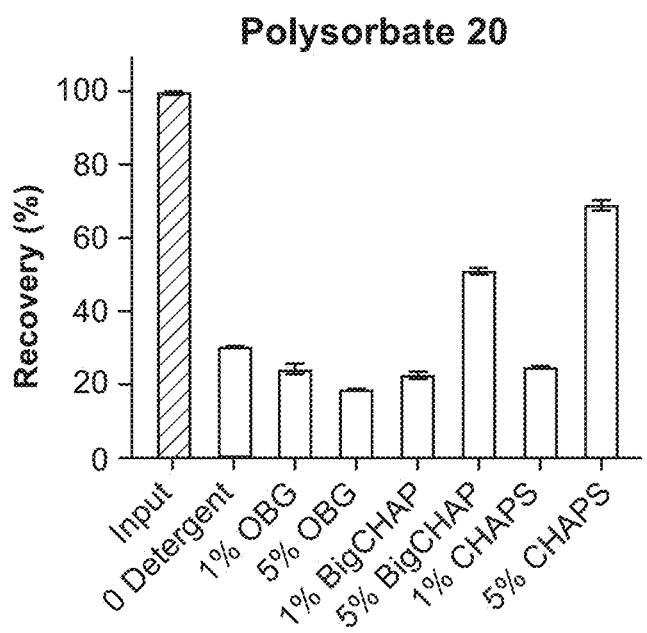
Figure 8B:
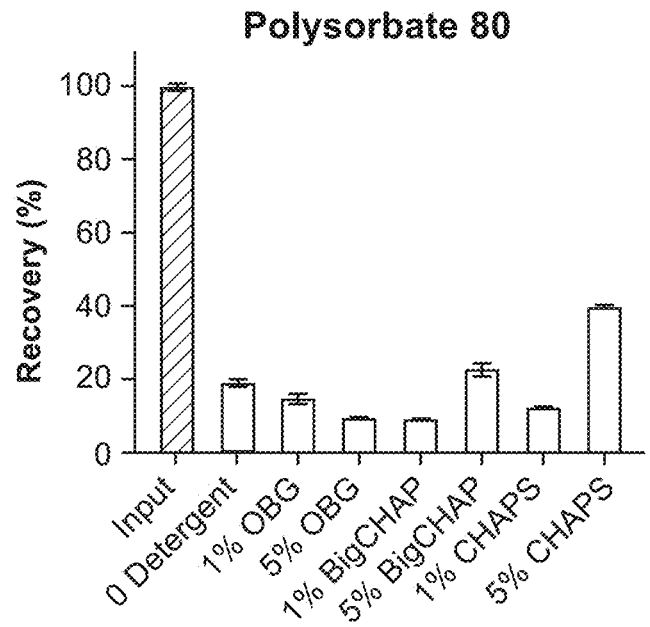
Figure 8B:
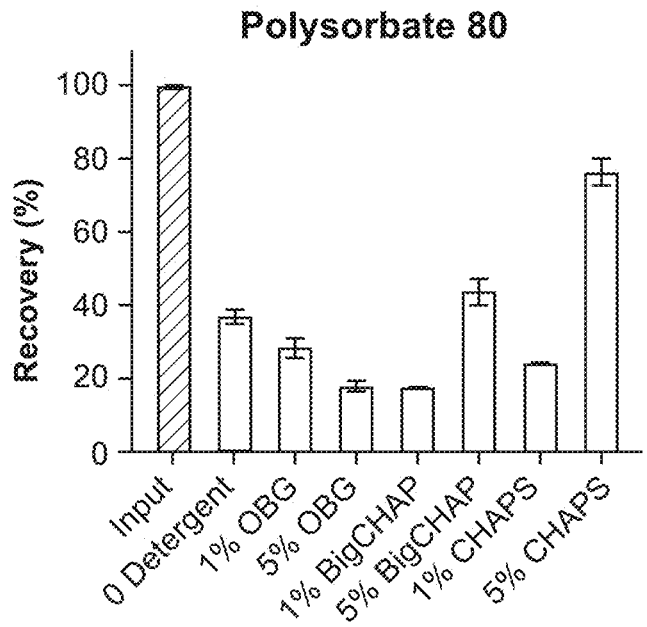
Figure 8C:
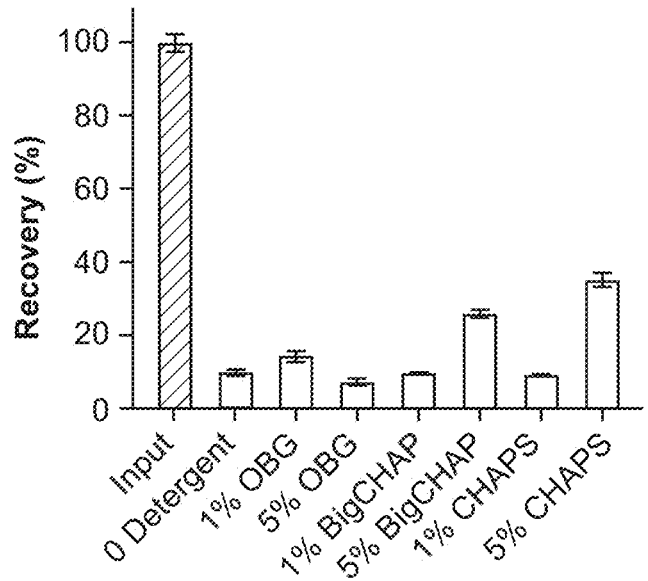
Figure 8C:
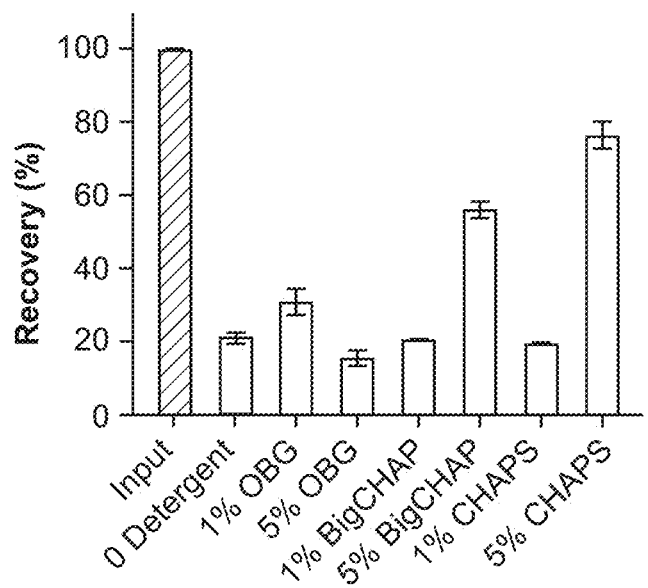

FIGS. 8A to 8C show the results of optimized mixed micelle extraction protocols developed for BoNT/A samples containing polysorbate 20, polysorbate 80, and Triton X-100 primary detergents, and using octyl-β-galactoside, Big-CHAP, and CHAPS as secondary detergents, as characterized using the BoTest A/E assay. Spin columns were pre-blocked with human serum albumin prior to use; human serum albumin was also added to the BoNT/A preparations. Surprisingly, Inventors have found that some primary detergents (e.g. Triton X-100) appear to be able to be removed from samples by diafiltration without the need for formation of mixed micelles. As shown, recovery of functional BoNT/A shows improvement with increasing concentration of secondary detergent for most primary/secondary detergent combinations.

While the BoTest™ A/E reagent, which is a solvated synthetic peptide, was used as a biochemical test to characterize recovery of BoNT/A in the above studies, in some applications cell-based assays can be used to characterize an analyte-containing sample from which a primary detergent has been removed by mixed micelle extraction. Such cell-based assays can have the advantage of providing an additional selectivity step in the form of selective uptake of the analyte. For example, Botulinum neurotoxins (such as BoNT/A) are selectively taken up by motor neurons and some neuron-derived cells in culture. Primary detergents used as excipients can adversely affect such cells.

An example of such interference is shown in FIG. 9A. Samples of purified BoNT/A holotoxin in surfactant-free media and similar concentrations of a commercial product that provides BoNT/A in a media containing a polysorbate 80 (P80) excipient were applied to the BioSentinel BoCell™ A/E cell-based assay, which utilizes cells genetically modified to express a BoNT/A sensitive reporting peptide that includes a FRET pair of fluorophores. Results of the emission ratio from these fluorophores relative to the log of BoNT/A concentration are shown in FIG. 9A. As shown, the cell based assay showed essentially no response to BoNT/A containing samples that included the surfactant. FIG. 9B shows the results of similar studies in which the samples were dialyzed prior to application to the cells. As shown, dialysis provides little improvement. While $EC_{50}$s were obtainable with the dialyzed samples the estimated values are approximately 10-fold higher than that obtained for BoNT/A provided in various surfactant-free media when applied to the same assay.

Accordingly, the utility of mixed micelle extraction in reducing primary detergent effects on cells in culture was characterized using cells and media utilized in the BoCell™ A/E assay and BoNT/A samples in iBAM2 cell culture media containing 0.1% polysorbate 80 as a surfactant excipient. Aliquots (100 μL) of this BoNT/A formulation were extracted with either 400 μL of 2% MEGA8 or 1% of other secondary surfactants, and the resulting mixtures concentrated using Amicon Ultra™ centrifugal filters. The resulting concentrate was washed with an additional 450 μL of the secondary surfactant solution by an additional round of centrifugation, followed by an additional wash with 450 μL of iBAM2 media. The resulting samples (app. 15 μL) were then adjusted to a volume of 100 μL with iBAM2 media and added to BoCell™ A/E cell containing wells of a culture plate. Cells were characterized imaged after 24 hours and 48 hours at 37° C. in 5% $CO_2$. Results at 48 hours are shown in FIG. 9C. In FIG. 9C cells that are visually similar to control cells are indicated with a star. As shown, MEGA 10, BIGCHAPS, and CHAPS gave results similar to untreated control cells and cells treated only with the BAM2 media. Inventors believe that preservation of normal cell distribution and morphology indicates successful removal of the polysorbate 80 excipient and preservation of cell health.

Studies were performed using samples containing various concentrations of BoNT/A in polysorbate 80-containing media, processed in the same manner using BIGCHAPS as the secondary surfactant, and applied to the BioSentinel BoCell™ BoNT A/E cell-based assay. Results were compared to those obtained with BoNT/A in a media that did not include the surfactant, and are shown in FIG. 9D. As shown, following mixed micelle extraction the surfactant-containing samples provide dose/response curves in cell-based BoNT/A assays that are very similar to those obtained from surfactant-free samples. A comparison of EC50 values obtained is provided in Table 1.

TABLE 1

| Test # | BoNT/A + P80 $EC_{50}$ (pM) | BoNT/A Control $EC_{50}$ (pM) | Relative Recovery (%) |
|---|---|---|---|
| 1 | 0.77 | 0.37 | 48.1% |
| 2 | 0.68 | 0.36 | 52.9% |
| 3 | 0.81 | 0.41 | 50.6% |

Overall, mean $EC_{50}$ obtained from surfactant-containing samples was 50.5% (CV 4.8%) of that obtained from control samples, which can be readily corrected for using an adjustment factor (e.g. 0.5).

Figure 10:
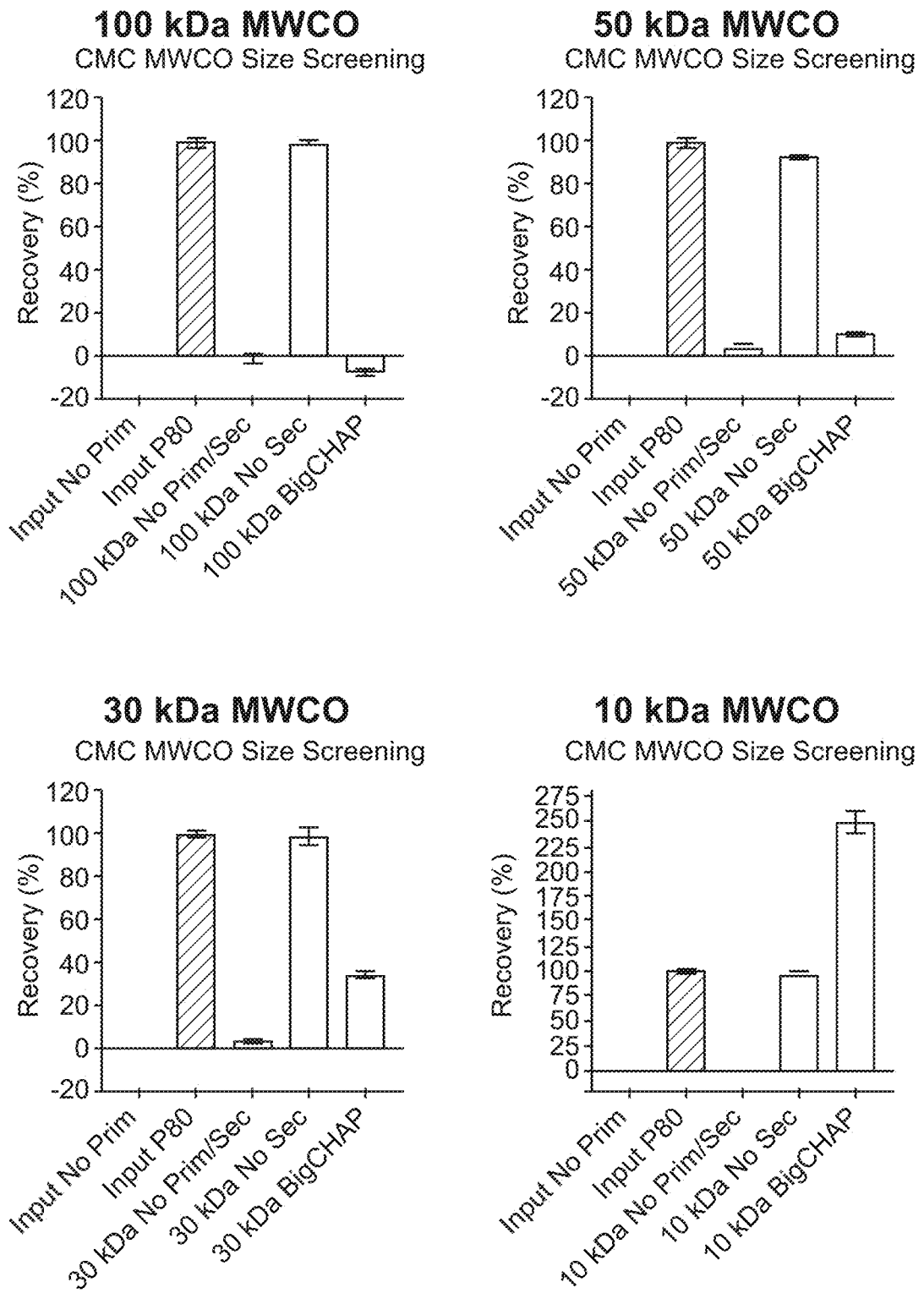
FIG. 10.

In the studies described above the ultrafiltration membranes utilized had a molecular weight cutoff (MWC) of 100 kDa. It should be appreciated, however, that it is possible for proteins of somewhat higher molecular weight (for example, BoNT/A at 150 kDa) to pass through such membranes owing to the shape of the protein molecule and distribution of membrane pore sizes. Accordingly, further studies were performed to characterize the effective range of MWC useful for mixed micelle removal of surfactants from solution. Studies were performed for passage of the polysorbate 80 (as the primary detergent) in the presence or absence of BIGCHAPS (as the secondary detergent). Material passing through regenerated cellulose ultrafiltration membranes was characterized using the CMC 535™ assay, which is responsive to polysorbate 80 but non-responsive to BigCHAP. The results are shown in FIG. 10. As shown both 100 kDa and 50 kDa molecular weight cutoff (MWC) regenerated cellulose ultrafilters permit passage of the mixed micelles, whereas the retentate shows increasing amounts of polysorbate 80 when 30 kDa and 10 kDa MWC ultrafilters are used.

Figure 11:
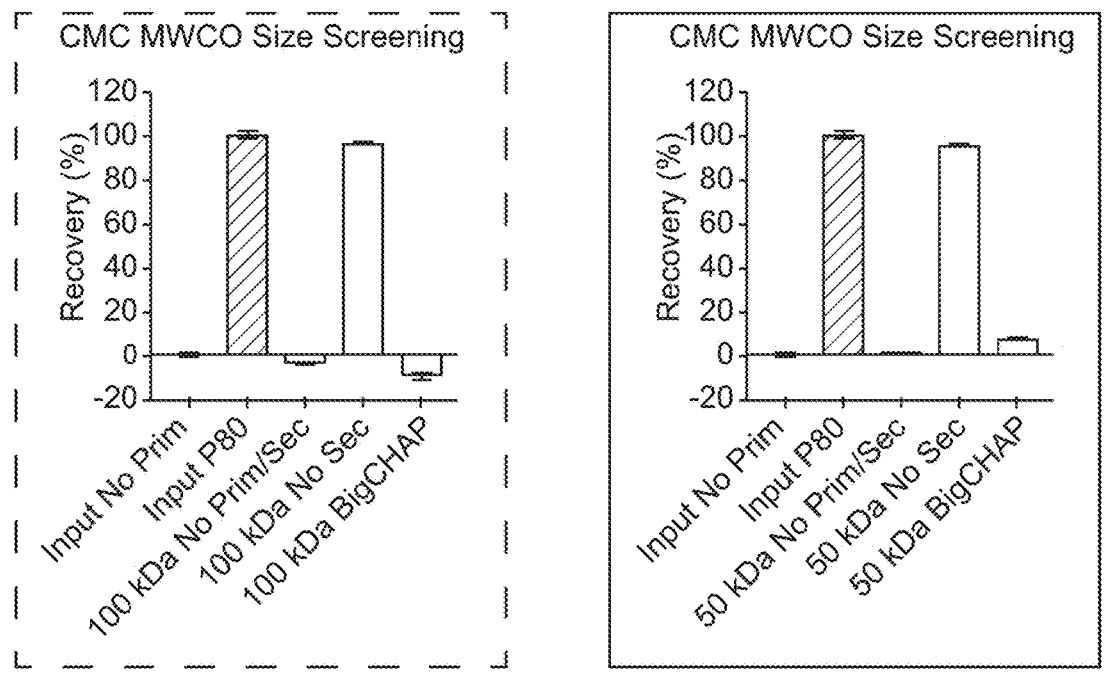
FIG. 11.
Figure 11:
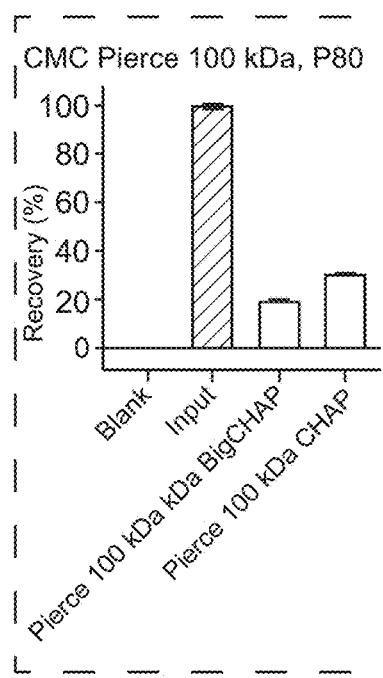
Figure 11:
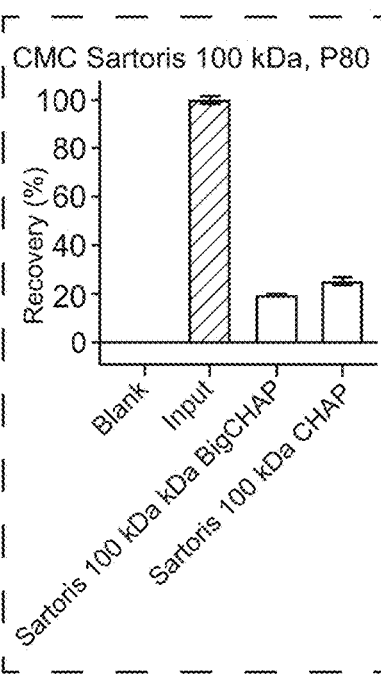
Figure 11:
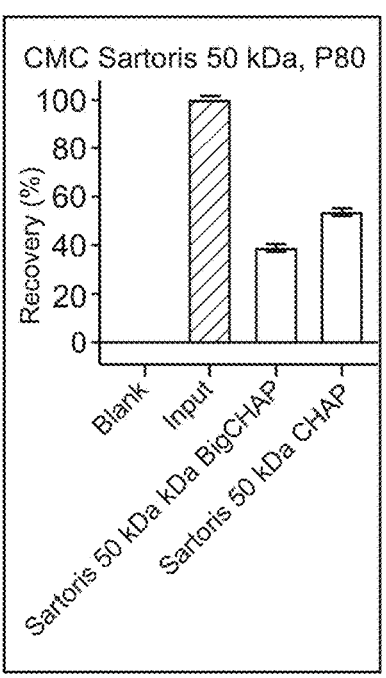

It should be appreciated that while regenerated cellulose filters are commonly used due to their high porosity and relatively low nonspecific binding, other materials used in ultrafiltration membranes (e.g. PES) are manufactured by different methods and may show different properties in regard to mixed micelle exclusion. Examples of results from studies performed using PES ultrafilters having different MWCs are shown in FIG. 11. As shown, PES membranes having 100 kDa and 50 kDa MWCs show significantly greater retention of the mixed micelles than regenerated cellulose membranes with similar nominal molecular weight cutoffs.

Figure 12:
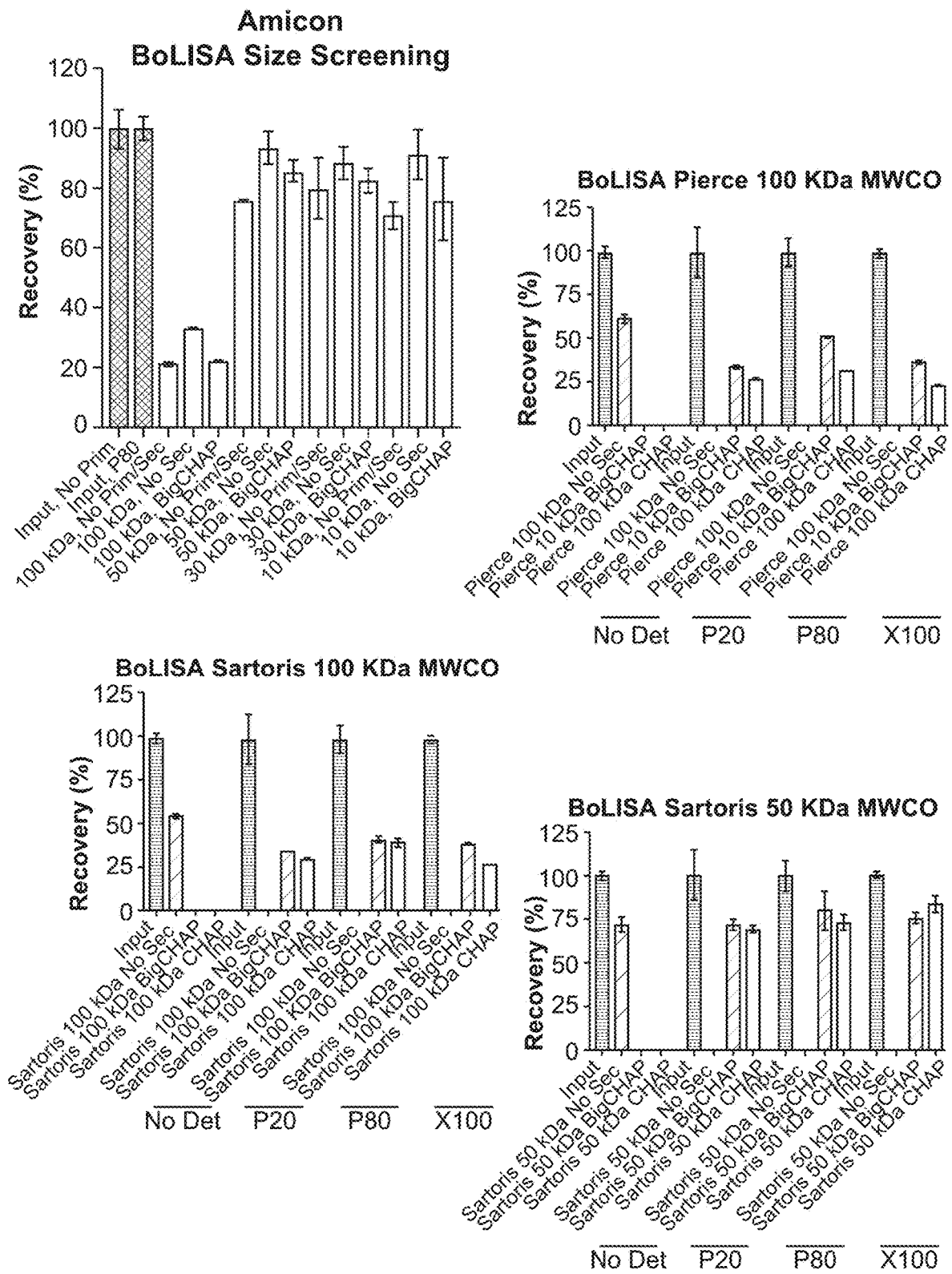
FIG. 12.

FIG. 12 shows the effect of different ultrafiltration membrane formulations on the recovery of BoNT/A from media containing polysorbate 80, using BigCHAP as the secondary detergent. The BoLISA™ assay is an immunological assay that is not impacted significantly by residual polysorbate 80, and was used to quantify BoNT/A in these studies. As shown, BoNT/A recovery is similar for both regenerated cellulose and PES ultrafiltration membranes, with somewhat lower recovery observed for PES.

In order to reduce nonspecific binding to ultrafiltration membranes and other surfaces it is a common practice to block available nonspecific binding sites on such surfaces using a protein such as casein, gelatin, ovalbumin, bovine serum albumin, human serum albumin, nonspecific immunoglobulin, etc. Such surfaces can be pre-blocked by treatment with protein prior to exposure to the sample being processed, blocked during processing by adding the protein into the sample being processed (typically as a small volume of concentrated stock solution), or both. Such blocking proteins, however, can have a negative impact on downstream processes such as characterization using in vitro methods (such as BoLISA™ and BoTest™) or cell-based assays (such as BoCell™).

Figure 13:
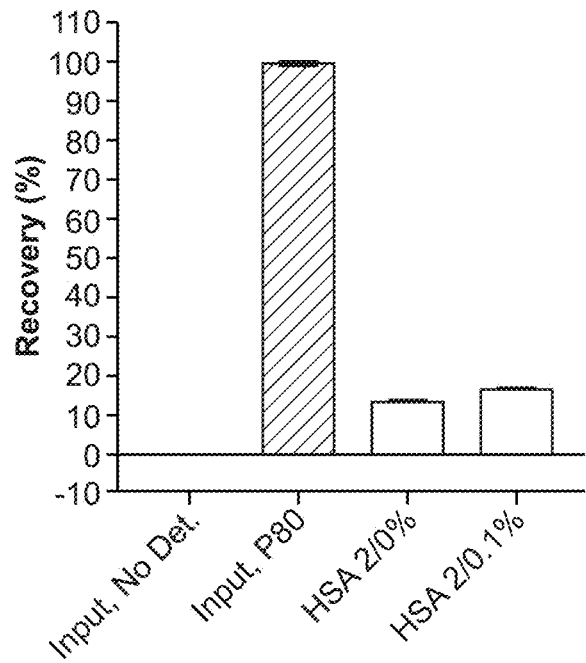
FIG. 13.
Figure 13:
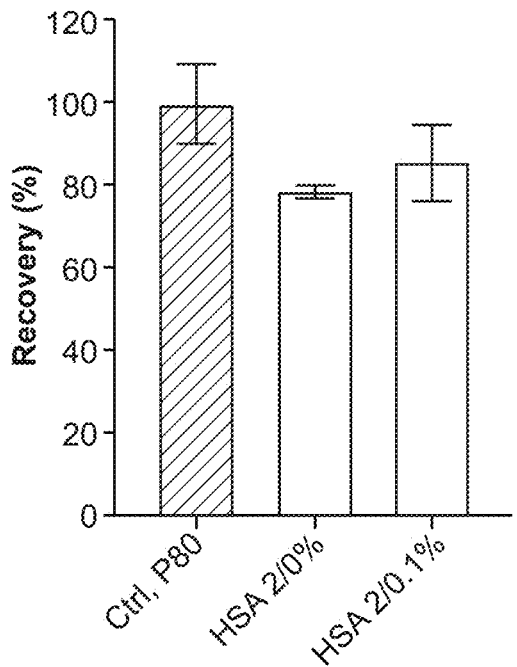
Figure 13:
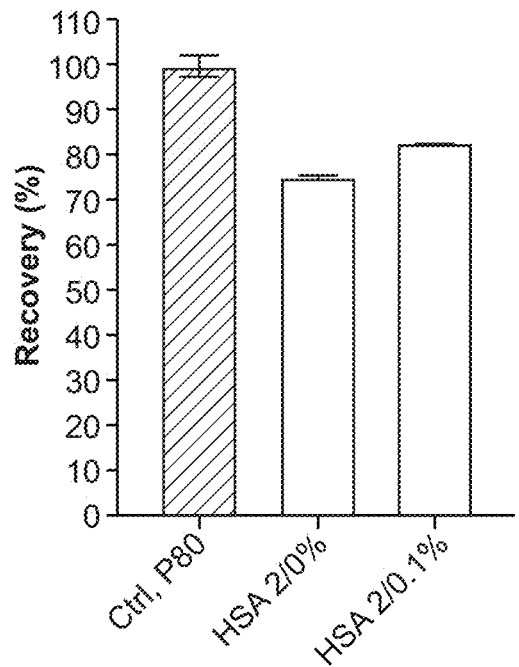

FIG. 13 shows the impact of pre-blocking ultrafiltration membranes used in mixed micelle processing with human serum albumin (2% w/v, overnight) and pre-blocking ultrafiltration membranes combined with spiking of human serum albumin into the sample being processed at 0.1% w/v. Samples were characterized for primary detergent content using the CMC 535™ assay, and for BoNT/A recovery using BoLISA™ and BoTest™ assays As shown, addition of human serum albumin to samples subsequently treated with pre-blocked ultrafiltration membranes had little impact on detergent removal, and slightly improved recovery of BoNT/A when characterized by the BoLISA™ and BoTest™ in vitro testing methodologies.

Figure 14:
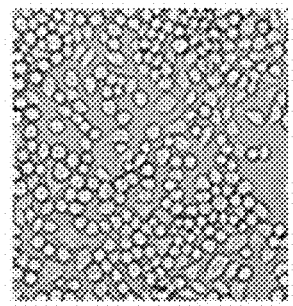
FIG. 14.
Figure 14:
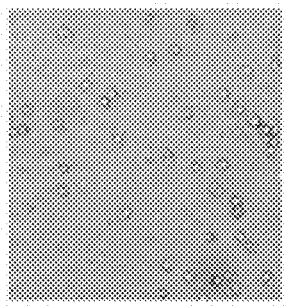
Figure 14:
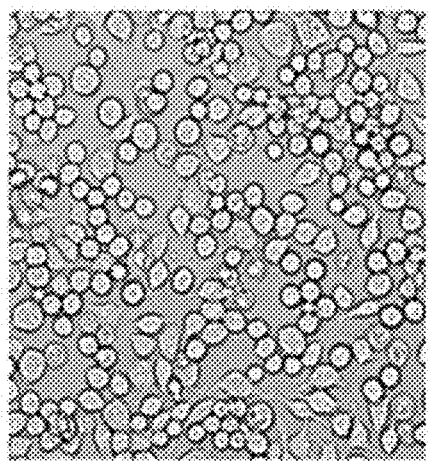
Figure 14:
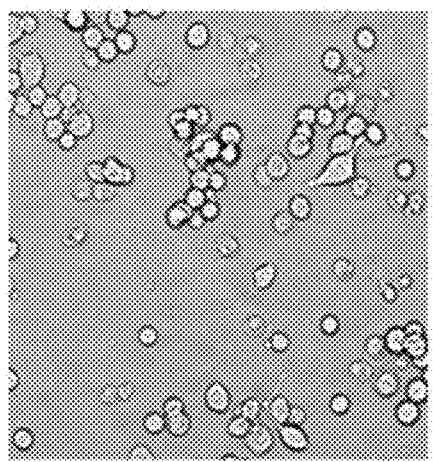

FIG. 14 shows the impact of adding human serum albumin to samples being characterized for BoNT/A content using the in vivo BioSentinel BoCell™ assay As shown, addition of human serum albumin to samples being treated using the mixed micelle method and pre-blocked ultrafiltration membranes had a negative impact on the health of cells used in the BoCell™ assay. Accordingly, the impact of blocking proteins added to samples processed by a mixed micelle separation method on downstream processes is process-dependent.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A system for removing a first surfactant or detergent from a solution, comprising:
    a protein having a first hydrodynamic radius;
    mixed micelles having a third hydrodynamic radius that is less than the first hydrodynamic radius, wherein the mixed micelles consist of the first surfactant or detergent and a second surfactant or detergent; and
    a separating device configured to separate the protein from the mixed micelles by a size-based separation method to generate a high molecular weight fraction comprising the protein and at least 80% depleted in the first surfactant relative to the first solution and a low molecular weight fraction comprising the mixed micelles.

2. The system of claim 1, wherein the separating device comprises an ultrafiltration membrane.

3. The system of claim 1, wherein the separation device comprises a gel filtration media.

4. The system of claim 1, wherein the first surfactant or detergent is selected from the group consisting of polysorbate 20, polysorbate 80, and Triton X-100.

5. The system of claim 1, wherein the second surfactant or detergent is selected from the group consisting of a galactoside detergent, a glucamide detergent, a cholamide detergents, and a sulfobetaine detergent.

6. The system of claim 5, wherein the galactoside detergent is octyl-β-galactoside.

7. The system of claim 5, wherein the glucamide detergent is selected from the group consisting of MEGA 8, MEGA 9, and MEGA 10.

8. The system of claim 5, wherein the cholamide detergent is selected from the group consisting of CHAPS, CHAPSO, and BIGCHAPS.

9. The system of claim 5, wherein the sulfobetaine detergent is sulfobetaine 3-10.

10. The system of claim 1, wherein the protein is a Botulinum neurotoxin.

11. The system of claim 1, wherein the Botulinum neurotoxin is Botulinum neurotoxin serotype A.

* * * * *